United States Patent
Miller et al.

(10) Patent No.: US 10,837,968 B2
(45) Date of Patent: Nov. 17, 2020

(54) PHOTOACTIVATABLE VOLTAGE SENSITIVE DYES

(71) Applicant: THE REGENTS OF THE UNIVERSITY OF CALIFORNIA, Oakland, CA (US)

(72) Inventors: Evan Miller, Berkeley, CA (US); Vincent Grenier, Berkeley, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 375 days.

(21) Appl. No.: 15/514,786

(22) PCT Filed: Oct. 1, 2015

(86) PCT No.: PCT/US2015/053600
§ 371 (c)(1),
(2) Date: Mar. 27, 2017

(87) PCT Pub. No.: WO2016/054442
PCT Pub. Date: Apr. 7, 2016

(65) Prior Publication Data
US 2017/0219595 A1    Aug. 3, 2017

Related U.S. Application Data

(60) Provisional application No. 62/058,578, filed on Oct. 1, 2014.

(51) Int. Cl.
| G01N 33/542 | (2006.01) |
| G01N 33/58 | (2006.01) |
| C07D 311/82 | (2006.01) |
| C09B 11/24 | (2006.01) |
| G01N 33/50 | (2006.01) |

(52) U.S. Cl.
CPC ......... *G01N 33/582* (2013.01); *C07D 311/82* (2013.01); *C09B 11/24* (2013.01); *G01N 33/502* (2013.01); *G01N 33/542* (2013.01); *Y02P 20/55* (2015.11)

(58) Field of Classification Search
CPC ............. G01N 33/542; G01N 21/6486; G01N 2500/10; G01N 33/5008; G01N 33/502; G01N 33/582; C09K 11/06; C09K 2211/1007; C09K 2211/1011; C09K 2211/1088; C07D 311/82; C09B 11/24; Y02P 20/55
See application file for complete search history.

(56) References Cited

FOREIGN PATENT DOCUMENTS

WO    WO 2012/159116    11/2012

OTHER PUBLICATIONS

Ellis-Davies, GCR (2007) Nature Methods 4(8): 619-628 (Year: 2007).*
Alivisatos, et al., Neuron, 74:970 (2012).
Alivisatos, et al., Science, 339:1284 (2013).
Connolly et al., Biosens Bioelectron 5(3):223-34 (1990).
Ellis-Davies, Nature Methods 4(8): 619 (2007).
Fast and Kleber, Cardiovasc Res 29(5):697-707 (1995).
Gee et al., Bioorg. Med. Chem. Lett. vol. 11, 2181-2183 (2001).
Grynkiewicz, et al., J Biol Chem, 260:3440 (1985).
Hinner, et al., Chembiochem, 7:495 (2006).
Insel, et al., Science, 340:687 (2013).
Jin, et al., Neuron, 75:779 (2012).
Miller, et al., Natl Acad Sci USA, 109:2114 (2012).
Ng, et al., ACS Chem Biol, 6:444 (2011).
Schackow et al., Am J Physiol 268(4 Pt 1):C1002-17 (1995).
St-Pierre, et al., Nat Neurosci, (2014).
Tsien, R. Y., Biochemistry-US, 19:2396 (1980).
Walsh et al., Neuroscience 69(3):915-29 (1995).
Zoran et al. Dev Biol 179(1):212-22) (1996).

* cited by examiner

*Primary Examiner* — Heidi Reese
(74) *Attorney, Agent, or Firm* — Morgan, Lewis & Bockius LLP; Jeffry S. Mann; Todd Esker

(57) ABSTRACT

Compounds and methods for determining transmembrane potential, monitoring changes in transmembrane potential, and/or drug screening are provided. In one aspect, compounds of the invention have a structure according to the formula: E-M-A-C*, wherein A is a fluorophore, selected from xanthenes, coumarins, cyanines, bimanes, and difluoroboradizaindacenes, charged at physiological pH; M is a molecular wire; and E is a hydrophobic moiety, wherein A and E are capable of being involved in a photo-induced, intramolecular electron transfer that quenches the fluorescence of A in response to a voltage condition. C* is a caging moiety (e.g., a photoremovable protecting group). When in use, exemplary compounds of the invention are membrane-impermeant and oriented within the cell membrane such that the charged moiety localizes at the outer leaflet of the lipid bilayer and the hydrophobic moiety and molecular wire associate with the hydrophobic portion of the lipid bilayer. The rate of electron transfer, fluorescence intensity, and quenching are altered in response to changes in transmembrane potential.

23 Claims, 12 Drawing Sheets

PHOTOACTIVATABLE VOLTAGE SENSITIVE DYES

SPONSORED RESEARCH OR DEVELOPMENT

This invention was made with Government support under Grant No. 4 R00NS078561 awarded by the NIH/NINDS. The Government has certain rights in the invention.

BACKGROUND OF THE INVENTION

Changes in neuronal membrane potential encode the vast range of thoughts, feelings, and behaviors that comprise the human experience. Despite the central importance of the brain to all of human health and disease, the molecular and cellular mechanisms underlying brain and neuronal function remain incompletely characterized, prompting efforts at the national and international level to develop a more comprehensive map of neuronal activity (Alivisatos, et al., Neuron, 2012, 74:970; Insel, et al., Science, 2013, 340:687; Alivisatos, et al., Science, 2013, 339:1284). Much of modern neurobiology stands upon the electrophysiological recordings of the activity of single neurons embedded within a network context. While this approach has proven incredibly powerful, real limitations exist, namely the invasive requirement of sticking an electrode into biological samples, severely disrupting underlying tissue, restricting recordings primarily to cellular soma, and making recording from multiple sites challenging or impossible.

Optical monitoring of electrical activity in the nervous system provides a powerful method for understanding brain function. In theory it can provide very precise measurements of the spatial and temporal dynamics of electrical activity in the brain. Currently methods to do this rely either on electrophysiology, which can provide extremely sensitive measurements of electrical activity in single neurons with good temporal resolution. Spatial information in a sub-cellular sense is difficult to acquire because of the requirement of bulky electrode. Information on populations of neurons is difficult to acquire because multiple electrode are required. Fluorescence imaging of $Ca^{2+}$ can provide spatial resolution at the sub- and supra-cellular level, but these signals are downstream of the action potential, difficult to resolve in fast spiking neurons, buffered by the indicators themselves, and biased toward post-threshold events. Although a variety of fluorescent probes for voltage have been developed, they suffer from either from low sensitivity or slow response times. Two major classes exist, fast and slow response dyes. Fast response dyes can temporally resolve action potentials, because they respond to voltage in the sub-microsecond time regime. However, the fractional changes can be very small (typically about 2-10%/100 mV). Slow response dyes redistribute themselves within the membrane in response to changes in membrane potential, and their concentration can change up to 10-fold in response to a Nernstian equilibrium, however, these large changes require movement of a charged dye molecule through the lipid membrane, resulting in slow response times and capacitive loading.

In contrast, a molecular wire electron transfer (eT) based optical probe provide large and fast changes in response to voltage with no capacitive loading. Increasing the sensitivity of the probe to voltage without sacrificing speed will increase its utility in monitoring voltage in brain systems. However, because small molecule dyes must be delivered to the systems of interest, i.e. they are not genetically encoded and therefore not synthesized by the cells, selective staining of neurons is not selective. As a result, signal-to-noise ratios for the measured optical changes can be quite small. Some genetically encoded voltage sensors exist, but are either too dim (Hochbaum, et al., Nat Methods, 2014), too insensitive (Mutoh, et al., ACS Chemical Neuroscience, 2012, 3:585), provide non-ideal turn-off responses to membrane depolarizations (St-Pierre, et al., Nat Neurosci, 2014; Jin, et al., Neuron, 2012, 75:779), or have the potential to add capacitive loads to membranes of interest (Mutoh, et al., ACS Chemical Neuroscience, 2012, 3:585; St-Pierre, et al., Nat Neurosci, 2014; Jin, et al., Neuron, 2012, 75:779). Small molecule dyes, in contrast are generally brighter, and VoltageFluors in particular are fast and sensitive enough to detect action potential spikes in single trials. Genetic targeting of VF dyes has not been achieved, and sparse labeling of neurons with VF dyes would increase the tractability of the approach for use in tissues, brain slices, and in vivo contexts.

Fluorescence imaging uniquely addresses this problem because the technique is non-invasive, can be applied to many cells simultaneously to provide spatial information on membrane potential changes, and can be high-throughput. Of available optical methods, $Ca^{2+}$ has been the chief surrogate for imaging neuronal activity, dating back to small molecule probes disclosed some 30 years ago (Tsien, R. Y., Biochemistry-US, 1980, 19:2396; Grynkiewicz, et al., J Biol Chem, 1985, 260:3440) and more recently with genetically encoded fluorescent protein sensors (Chen, et al., Nature, 2013, 499:295). However, $Ca^{2+}$ imaging's primary limitation is that it provides only an inference of the underlying membrane potential change, since $Ca^{2+}$ entry into the neuronal cytosol is controlled by voltage-gated ion channels that only become activated during the later portion of an action potential. Additionally, buffering by endogenous ligands and the extended rise in intracellular $Ca^{2+}$ (on the order of 100 s of milliseconds) make resolving individual spikes difficult in some contexts and provides no information regarding sub-threshold changes in membrane potential.

Therefore, voltage imaging remains an attractive solution because it can provide the direct measurement of membrane voltage achieved through electrophysiology while providing the spatial resolution, throughput, and parallel recording capabilities of $Ca^{2+}$ imaging approaches. Recently, voltage-sensitive small molecules based on molecular wires emerged as an intriguing class of fluorophores for voltage sensing (Miller, et al., Natl Acad Sci USA, 2012, 109:2114; Miller, et al., University of California, USA, 2012, WO2012159116A2, 102 pp). These VoltageFluors, or VF dyes, sense changes in transmembrane potential by a photoinduced electron transfer (PeT) mechanism. PeT from an electron-rich aniline through a molecular wire to a fluorescent reporter is controlled by the electric field across the plasma membrane of an excitable cell, a neuron for example. At rest, where typical mammalian neuronal membrane potentials are approximately −60 mV inside the cell, PeT is enhanced, resulting in diminished fluorescence. As the membrane depolarizes—during an action potential or upon integration of excitatory inputs from connected neurons—PeT decreases, resulting in enhanced fluorescence. Consequently, VF dyes display large voltage-sensitive change in fluorescence, approximately 27% ΔF/F per 100 mV—nearly 2.5× greater than the most readily available voltage sensitive dyes—while maintaining the fast response time needed for resolving single action potential spikes. Importantly, because PeT within the VoltageFluor scaffold is fast compared to the biological event of interest, VF dyes add no capacitive load, making them ideal candidates for non-disruptive sensors of neuronal activity.

Despite these important characteristics, the amphipathic nature of VF dyes results in non-specific uptake into all plasma membranes within a biological sample, obscuring the boundary between adjacent stained cells and making it difficult to detect voltage-induced fluorescence changes against a high background of non-excitable cells stained with the dye.

In view of the above drawbacks, methods and compositions are needed which are sensitive to small variations in transmembrane potentials and can respond both to rapid, preferably on a millisecond timescale, and sustained membrane potential changes. Also needed are methods and compositions less susceptible to capacitative loading issues and capable of providing a ratiometric fluorescence signal.

The ability to sparsely label neurons of cells with VF dyes would address this problem in much the same way that the sparse labeling efficiency of the Golgi stain enabled the beautiful reconstruction of neuronal morphology by Ramon y Cajal over a century ago. The present invention provides compositions and methods for sparsely labeling neurons of cells with VF dyes.

BRIEF SUMMARY OF THE INVENTION

Exemplary compositions and methods of the present invention provide a combination of sub-type specificity achieved through spatially-defined patterns of illumination, coupled with the fast, sensitive, and non-capacitive voltage sensing characteristics of VoltageFluors. Thus, the present invention provides useful compounds and methods for interrogating neuronal systems.

In various embodiments, the invention provides voltage sensitive dyes chemically modified to improve their localization and signal-to-noise in complex biological preparations. In an exemplary embodiment, the invention provides methods for the design, synthesis, and imaging applications of small-molecule ehotoactivatable ptical sensors of transmembrane potential (SPOT).

SPOT localizes to cell membranes and remains non-fluorescent until activated with light. Illumination efficiently generates the parent VF dye which can then optically report on changes in the membrane voltage. Because of the large fluorescence increase upon illumination, SPOT provides a simple method for targeting neurons of interest within complex biological samples, improving resolution and signal to noise compared to non-targeted loading of VF dyes.

In an exemplary embodiment, after illumination, SPOT behaves substantially similarly, or even identically, to the parent VF sensor, yielding an optical voltage sensitivity of approximately 25% ΔF/F per 100 mV in HEK cells.

In an exemplary embodiment, SPOT enables sub-type selective staining of neurons by spatially restricting uncaging to cells expressing a complementary lable, e.g., an mCherry label.

In an exemplary embodiment, SPOT enables detection of single spikes with cellular resolution.

In an exemplary embodiment, the invention provides compounds according to Formula I:

$$E\text{-}M\text{-}A\text{-}C^* \quad (I)$$

wherein A is a fluorophore, e.g., selected from xanthenes, coumarins, cyanines, and bimanes. A is optionally charged at physiological pH. M is a molecular wire. E is a substituted aryl or substituted heteroaryl moiety, which is substituted with an electron donating or electron withdrawing moiety. Following photoactivation leading to cleavage of caging moiety, C*, from the compound, A and E are capable of being involved in a photo-induced electron transfer generating fluorescence from A in response to a voltage condition.

In an exemplary embodiment, SPOT is based upon modification of an established voltage-sensitive dye, Voltage-Fluor—or VF—capped with caging group (e.g., a dimethoxy-o-nitrobenzyl caging group) to essentially eliminate fluorescence of the VF dye prior to uncaging.

VF dyes have already been shown to be valuable tools for measuring changes in transmembrane potential in neurons, cardiomyocytes, and pancreatic preparations. VF dyes sense changes in voltage with high speed (<ms response time), high sensitivity (~20-50% change in fluorescence per 100 mV), and no capacitive load, enabling VF dyes to detect action potentials, sub-threshold changes, and inhibitory currents in single trials in live cells.

In various embodiments of the current invention, SPOT, localizes to cell membranes and remains non-fluorescent until activated with light. Illumination efficiently uncages the SPOT compound according to Formula I, generating the parent VF dye which can then optically report on changes in the membrane voltage. Because of the large fluorescence increase upon illumination, SPOT provides a simple method for targeting neurons of interest within complex biological samples, improving resolution and signal to noise compared to non-targeted loading of VF dyes.

In various embodiments, SPOT enables sub-type selective staining of neurons by spatially restricting uncaging to cells expressing a complementary label, e.g., a mCherry label. The combination of sub-type specificity achieved through spatially-defined patterns of illumination, coupled with the fast, sensitive, and non-capacitive voltage sensing characteristics of VoltageFluors makes SPOT a useful tool for interrogating neuronal systems.

Additional embodiments, objects and advantages of the present invention are apparent from the detailed description set forth below.

DETAILED DESCRIPTION OF THE INVENTION

Introduction

Figure 1A:
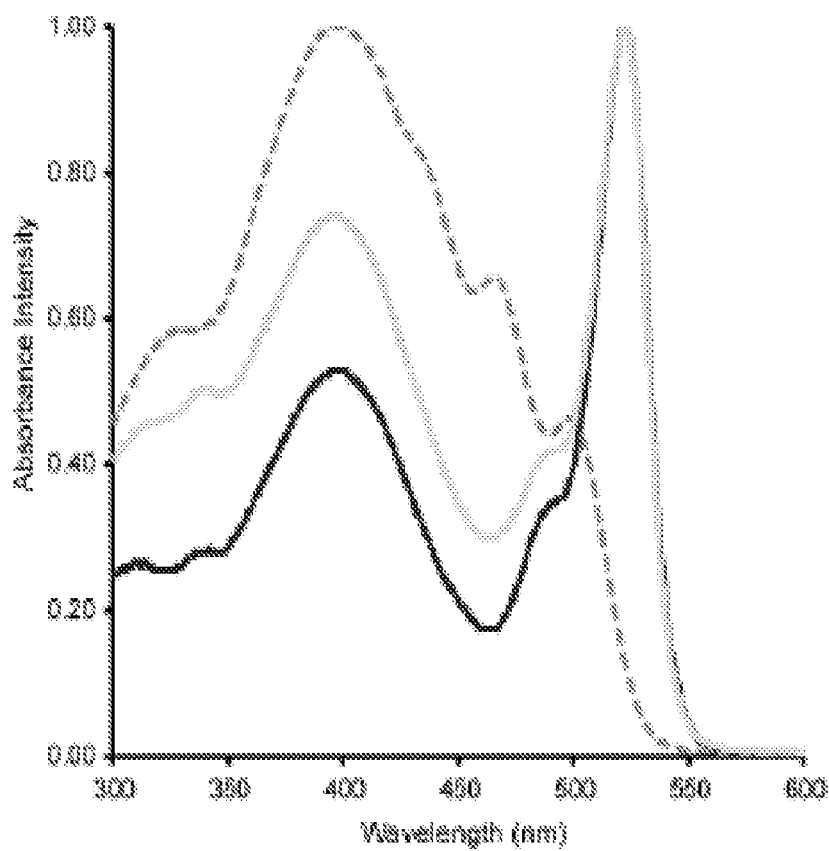
FIGS. 1A-1E. Illumination of SPOT dramatically increases fluorescence. Spectroscopic characterization of SPOT in PBS, pH 7. a) Absorbance profile of SPOT before (grey dotted trace) and after (green trace) illumination at 365 nm. The UV-vis spectrum of photoactivated SPOT is identical to a known standard of VF2.1.C1 (black trace). b) Emission spectrum of SPOT before (grey dotted trace) and after illumination (green trace) at 365 nm. c) HEK cells loaded with 200 nM SPOT prior to illumination. d) Cells from c) after illumination with 390 nm light for 30 seconds. e) Quantification of cellular fluorescence from cells stained with SPOT pre- and post-UV photoactivation. Illumination as in panel d) gives a 12-fold increase in fluorescence intensity (n=3).

Restricted labeling of a sub-set of neurons improves signal-to-noise by lowering background fluorescence and enables optical voltage recording with single cell/single spike resolution in tissue and in vivo. To achieve selective labeling of only a fraction of defined neurons, the present invention provides compounds and methods in which VF fluorescence is quenched ("caged") with a photolabile protecting group. The caged VoltageFluor would localize to cell membranes and remain non-fluorescent until uncaging or photoactivation via illumination liberated the parent VF fluorophores. Restricting uncaging illumination by scanning a region of interest (ROI) or through spatial light modulation (SLM) technology would provide fluorescent labeling of sub-populations of defined neurons. The only other existing method for targeting small molecule voltage sensors relies on over-expression of a membrane-targeted alkaline phosphatase that removes the phosphate groups on a modified voltage sensitive dye to increase membrane localization of the dye. Drawbacks of this approach include the use of buffers at high pH to effectively incorporate the dye, restricting the method's broad application (Hinner, et al., *Chembiochem*, 2006, 7:495; Ng, et al., *ACS Chem Biol* 2011, 6:444).

The disclosure hereinbelow sets forth the design, synthesis, and application of exemplary caged SPOT compounds according to Formula I as a first class of voltage sensing fluorophores that can be targeted to cells of interest via selective photo-uncaging.

Definitions

The term "membrane potential" or "transmembrane potential" refers to the electric potential difference across the membrane of a cell. The membrane may be selected from a plasma membrane, mitochondrial membrane, and a chloroplast membrane. In preferred embodiments, the membrane is a plasma membrane.

A "fluorophore" refers to a molecule or molecular moiety that emits fluorescence.

A "moiety" refers to a radical of a molecule that is attached to the remainder of the molecule.

The term "molecular wire," in the context of the present invention, refers to a molecular moiety that permits the flow of electrons from one end to the other end of the moiety. In some embodiments of the invention, the molecular wire employed is not an electroactive polymers, which themselves may donate or accept electrons. In various embodiments of the invention, the molecular wire is not a nucleic acid. In still other embodiments, the molecular wire is neither an electroactive polymer nor a nucleic acid. In exemplary embodiments, the molecular wire has substantially overlapping π-orbitals, i.e. conjugated π-orbitals, as between the monomeric units of the molecular wire, although the molecular wire may also contain other types of molecular orbitals. In some embodiments, the molecular wire of the invention is capable of transferring electrons at 100 Hz.

In an exemplary embodiment, the molecular wire of the present invention has a conductivity, S, of from between about $10^{-6}$ to about $10^4$ $\Omega^{-1}cm^1$, with from about $10^{-5}$ to about $10^3$ $\Omega^{-1}$ $cm^{-1}$ being preferred, with these S values being calculated for molecules ranging from about 20Å to about 200 Å. As described below insulators have a conductivity S of about $10^{-7}$ $\Omega^{-1}$ $cm^{-1}$ or lower, with less than about $10^{-8}$ $\Omega^{-1}$ $cm^{-1}$ being preferred. See generally Gardner et al., Sensors and Actuators A 51 (1995) 57-66, incorporated herein by reference.

As used herein, a "quencher" or "quenching group" refers to a molecular entity or group within a molecular entity, respectively, that can attenuate at least partly the light emitted by a fluorophore or fluorescent group. This attenuation is referred to herein as "quenching". Hence, illumination of the fluorescent group in the presence of the quenching group leads to an emission signal of lower intensity than would otherwise occur in the absence of the quenching group, or the absence of an emission signal. Quenching can occur by mechanism of energy transfer, charge transfer, intersystem crossing, electron exchange, photo-induced electron transfer, or chemical reaction.

As used herein, "caging moiety" refers to any fluorescence-modifying moiety of a compound of the invention that can attenuate, at least partly, the energy (e.g., light) emitted by a fluorescent dye. This attenuation is referred to herein as "quenching". In an exemplary embodiment, the caging moiety is a photoremovable protecting group. Hence, irradiation of the compound of the invention having an intact caging moiety leads to cleavage of the caging moiety from the flurorophore moiety of the compound and an emission signal from the fluorophore. Quenching of fluorescence through caging the fluorophore typically occurs through energy transfer between the fluorophore and the caging moiety. Examplary caging moieties and the principles behind the operation of such moieties are disclosed in Liss-Davies, *Nature Methods* 4(8): 619 (2007).

In quenching by photo-induced electron transfer (PeT), there is an electron donor and an electron acceptor and the excited fluorophore can be either the electron donor or electron acceptor. Where the excited state of a fluorophore acts as an electron acceptor, an electron-rich species can donate electron(s) to the photo-induced electron acceptor and thereby quench the fluorescence of the fluorophore. Alternatively, PeT quenching can also occur by electron transfer from the excited fluorophore to the quencher, e.g. an electron-deficient species, an electronegative halocarbon, etc. See *Principles of Fluorescence Spectroscopy*, 3ed. (2006) by Joseph Lakowicz, Springer Science+Business Media, LLC: New York. In both forms of PeT, the extra electron on the acceptor is returned to the electron donor.

The term "voltage condition," in the context of the present invention, is used in reference to the voltage condition of a cell membrane. Examples of membrane voltage conditions may range from the resting potential characteristic of a given cell in some embodiments to a transmembrane potential falling within an action potential of a given cell, e.g. between hypolarized state to depolarized state.

An "excitable cell type," as used herein, refers to a cell type capable of generating action potentials. Exemplary excitable cell types include, without limitation, nerve cells, endocrine secretory cells, neuroendocrine secretory cells, and muscle cells. The cells may be primary cultures that are set up for short term growth. Such primary cultures can provide highly reproducible results from one culture to another. Alternatively, cell lines are used. Cell lines are generally able to be passaged in culture for extended periods of time. They include, without limit, immortalized cells, stem cells, etc., where the stem cells are able to differentiate into excitable cells suitable for the subject methods. Examples of cultured excitable cells include, but are not limited to, suprachiasmatic neurons (Walsh et al. (1995) *Neuroscience* 69(3):915-29); motoneuronal cultures (Zoran et al. (1996) *Dev Biol* 179(1):212-22); cardiac tissue (Fast and Kleber (1995) *Cardiovasc Res* 29(5):697-707); cardiac ventricular myocytes; Schackow et al. (1995) *Am J Physiol* 268(4 Pt 1):C1002-17; electrogenic myocardiac cells (Connolly et al. (1990) *Biosens Bioelectron* 5(3):223-34).

A "control" sample or value refers to a sample or value that serves as a reference, usually a known reference, for comparison to a test sample or value. For example, in the context of the present invention, a control value for the transmembrane potential of a given cell type can be an average value gathered from a population of cells of that specific cell type, e.g., HEK, neuronal cell. One of skill in the art will understand which controls are valuable in a given situation and be able to analyze data based on comparisons to control values. Controls are also valuable for determining the significance of data. For example, if values for a given parameter vary widely in controls, variation in test samples will not be considered as significant.

The term "voltage clamp" or "voltage-clamped," refers to a biophysical technique which allows one to control the potential across a cell membrane with a feedback amplifier. For a review of commonly known voltage clamp methods, see *Microelectrode Techniques*, Ogden D (ed.) Cambridge (1987): Chapter 2—Voltage clamp techniques, by Halliwell et al.

A "cell membrane" or "cellular membrane," in the context of the present invention, refers to a plasma membrane or the membrane of any cellular organelle, such as the Golgi, mitochondria, chloroplast, and endoplasmic reticulum. In preferred embodiments, the cell membrane refers to the plasma membrane.

The "inner layer" of a cell membrane, as used herein, refers to the one of two leaflets in a cellular membrane which has a hydrophilic surface directed away from the extracellular environment. To illustrate, the inner layer of a plasma membrane refers to the cytosolic leaflet.

The "outer layer" of a cell membrane, as used herein, refers to the one of two leaflets in a cellular membrane which has a hydrophilic surface directed towards the extracellular environment. To illustrate, the outer layer of a plasma membrane refers to the exoplasmic leaflet.

In some embodiments, the compounds herein additionally include a "localization sequence," "targeting sequence," or "targeting moiety" to direct the compound to a particular organelle or cellular membrane of the cell. Targeting moieties and other molecular moieties useful in the present invention can include those known in the art, such as in WO/2001/04221.

"Targeting moiety," as used herein refers to any molecule to which a compound of the invention, or a conjugate incorporating a compound of the invention, is attached. Representative targeting moieties include a nucleic acid, protein (e.g., enzyme, antibody), glycoprotein, peptide, saccharide (e.g., mono-, oligo-, and poly-saccharides), hormone, receptor, antigen, substrate, metabolite, transition state analog, cofactor, inhibitor, drug, dye, nutrient, growth factor, etc., without limitation. "Targeting moiety" also refers to species that might not be considered to fall within the classical definition of "a molecule," e.g., solid support (e.g., synthesis support, chromatographic support, membrane), virus and microorganism. Exemplary conjugates of the invention including a targeting moiety are conjugated by covalent binding of the fluorophore to a linker and hence to a targeting moiety.

The term "agent" as used herein, describes any molecule. Candidate agents that can be employed with the screening methods described herein can encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including nucleic acids, e.g. ribozymes, deoxyribozymes, peptides, saccharides, fatty acids, steroids, purines, pyrimidines, derivatives, structural analogs or any combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain hydrocarbon radical, which may be fully saturated, mono- or polyunsaturated and includes mono-, di- (i.e., alkylene) and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups that are limited to hydrocarbon groups are termed "homoalkyl".

Typically, an alkyl group will have from 1 to 24 carbon atoms, with those groups having 10 or fewer carbon atoms being preferred in the present invention. A "lower alkyl" is a shorter chain alkyl, generally having eight or fewer carbon atoms. In some embodiments, alkyl refers to an alkyl selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroalkyl," by itself or in combination with another term, means, unless otherwise stated, a stable straight or branched chain, mono-, di- (i.e., heteroalkylene) and multivalent radicals consisting of carbon and at least one heteroatom selected from the group consisting of O, N, Si and S, and wherein the nitrogen and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "acyl" refers to a species that includes the moiety —C(O)R, where R has the meaning defined herein.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" includes trifluoromethyl, 2,2,2-trifluoroethyl, 4-chlorobutyl, 3-bromopropyl, and the like.

The term "aryl" means, unless otherwise stated, a polyunsaturated, aromatic, mono-, di- (i.e., arylene) and multivalent radicals that can be a single ring or multiple rings (preferably from 1 to 3 rings), which are fused together or linked covalently. The term "heteroaryl" refers to an aryl group (or ring) that contains from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

In some embodiments, any of alkyl, heteroalkyl, cycloalkyl, heterocycloalkyl, aryl and heteroaryl is optionally substituted. That is, in some embodiments, any of these groups is substituted or unsubstituted. In some embodiments, substituents for each type of radical are selected from those provided below.

Substituents for the alkyl and heteroalkyl radicals are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', —halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R", —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted heterocycloalkyl, substituted or unsubstituted aryl, substituted or unsubstituted heteroaryl, halogen, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted (C$_1$-C$_6$)alkyl.

The term "heteroatom" includes oxygen (O), nitrogen (N), sulfur (S) and silicon (Si).

The symbol "R" is a general abbreviation that represents a substituent group that is selected from acyl, alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl and substituted heteroaryl.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. In some embodiments, the definition of terms used herein is according to IUPAC.

Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The Embodiments

In an exemplary embodiment, the invention provides compounds according to Formula I:

$$E-M-A-C^* \quad (I)$$

wherein A is a fluorophore, e.g., selected from xanthenes, coumarins, cyanines, and bimanes. A is optionally charged at physiological pH. M is a molecular wire. E is substituted aryl or substituted heteroaryl moiety, which is substituted with an electron donating or electron withdrawing moiety. Following photoactivation leading to cleavage of caging moiety, C*, from the compound, A and E are capable of being involved in a photo-induced electron transfer generating fluorescence from A in response to a voltage condition.

The precursor to fluorophore, A, includes at least one moiety capable of forming a covalent bond with moiety of complementary reactivity on a precursor for C*. Such moieties are referred to herein as "reactive functional groups".

In some embodiments, A is an electron acceptor and E is an electron donor in said photo-induced electron transfer.

In some embodiments, A is an electron donor and E is an electron acceptor in said photo-induced electron transfer.

In some embodiments, A is negatively charged at physiological pH.

Table 1 provides exemplary fluorophore moieties of use in compounds of the invention.

TABLE 1

Exemplary Fluorophore Moieties for Compounds of the Invention 4-acetamido-4'-isothiocyanatostilbene-2,2'disulfonic acid
acridine and derivatives:
    acridine
    acridine isothiocyanate TABLE 1-continued Exemplary Fluorophore Moieties for Compounds of the Invention 5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
    coumarin
        7-amino-4-methylcoumarin (AMC, Coumarin 120)
        7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
    sulfonyl chloride derivative of sulforhodamine 101 (Texas Red)
    N,N,N',N'-tetramethyl-6-carboxyrhodamine (TAMRA)
    tetramethyl rhodamine
    tetramethyl rhodamine isothiocyanate (TRITC)
riboflavin
rosolic acid
terbium chelate derivatives There is a great deal of practical guidance available in the literature for functionalizing fluorophores and selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

There is a great deal of practical guidance available in the literature for functionalizing fluorophores and selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive functional groups, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

In some embodiments, A is selected from xanthenes.

In some embodiments, A has a structure according to the formula:

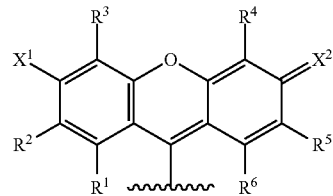

wherein $R^1$, $R^2$, $R^3$, $R^4$, $R^5$, and $R^6$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $X^1$ is selected from $Z^2R^{12}$ and $NR^{11}R^{12}$. $X^2$ is selected from $NR^{13}R^{14}$ and O. $R^{12}$ is selected from H, alkyl, substituted alkyl, heteroalkyl, substituted heteroalkyl, and $C(Z^3)R^5$. $R^{13}$ and $R^{15}$ are independently selected from alkyl, substituted alkyl, heteroalkyl, substituted heteroalkyl, $OR^{16}$ and $NR^{17}R^{18}$. $R^{16}$ is selected from H, alkyl, substituted alkyl, heteroalkyl, substituted heteroalkyl, aryl, substituted aryl, heteroaryl, substituted heteroaryl and $C(O)R^{19}$. $R^{19}$ is selected from alkyl, substituted alkyl, heteroalkyl and substituted heteroalkyl. $R^{11}$, $R^{13}$, $R^{14}$, $R^{17}$ and $R^{18}$ are independently selected from H, alkyl, substituted alkyl, heteroalkyl and substituted heteroalkyl. $Z^1$ and $Z^3$ are independently selected from O, S and NH. $Z^2$ is selected from O and S.

In some embodiments, A has a structure according to the formula:

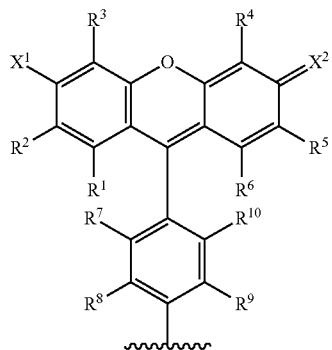

wherein $R^7$, $R^8$, $R^9$, and $R^{10}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $R^{11}$, $R^{12}$, $R^{13}$, $Z^1$, and $Z^2$ are as defined herein.

In some embodiments, $X^1$ is OH, $X^2$ is O, $R^2$ is Cl, $R^5$ is Cl and $R^{10}$ is $SO_3H$.

In some embodiments, $R^1$, $R^3$, $R^4$, and $R^6$ are H.

In some embodiments, $R^7$, $R^8$ and $R^9$ are H.

In some embodiments, E is selected from a substituted aryl and substituted heteroaryl.

In some embodiments, E is phenyl substituted with an amine.

The precursor to the xanthene moiety of a compound of the invention, includes at least one moiety capable of forming a covalent bond with moiety of complementary reactivity on a precursor for C*. Such moieties are referred to herein as "reactive functional groups".

In some embodiments, E has the structure according to the formula:

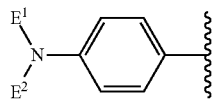

wherein $E^1$ and $E^2$ are independently alkyl. In some embodiments, $E^1$ and $E^2$ are independently selected from unsubstituted $C_1$-$C_6$ alkyl. In some embodiments, $E^1$ and $E^2$ are independently selected from methyl and butyl. In some embodiments, $E_1$ and $E_2$ are butyl.

In some embodiments, the butyl is n-butyl.

In some embodiments, M is selected from alkylene, substituted alkylene, heteroalkylene, substituted heteroalkylene, arylene, substituted arylene, heteroarylene and substituted heteroarylene.

In some embodiments, M has a structure according to the formula:

$$(-M^1-M^2-)_m-(M^1)_n$$

wherein $M^1$ is alkylene; $M^2$ is arylene; m is an integer selected from 0, 1, 2, 3, 4, 5, 6, 7, 8, 9, 10, 11, 12, 13, 14, 15, 16, 17, 18, 19 and 20; n is an integer selected from 0 and 1; and at least one of m and n is greater than 0.

In some embodiments, M has a structure according to the formula:

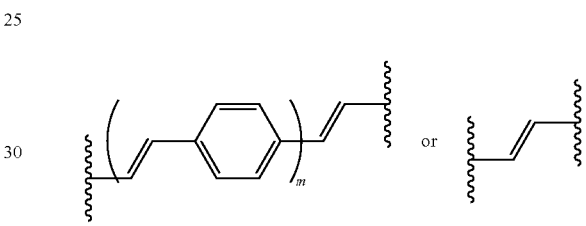

wherein m is an integer selected from 0, 1, 2, 3, 4, 5, 6, 7, 8, 9, 10, 11, 12, 13, 14, 15, 16, 17, 18, 19 and 20.

In some embodiments, M is a conjugated system.

In some embodiments, M is hydrophobic.

In some embodiments, the compound has a structure selected from:

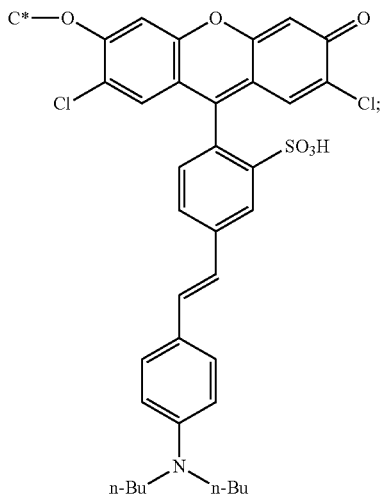

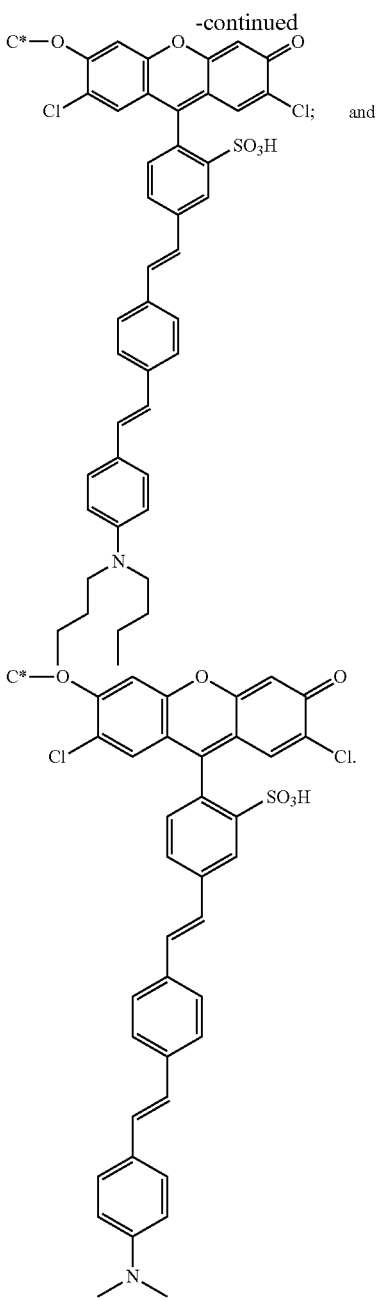

Exemplary C* moieties are photoremovable protecting moieties. An exemplary C*substituted alkyl, moiety has the structure:

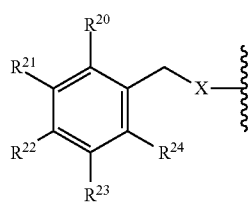

(II)

in which $R^{20}$, $R^{21}$, $R^{22}$, $R^{23}$, and $R^{24}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, acyl, H, $NO_2$, CN, $SO_3H$, $NR^{25}R^{26}$, $C(Z^4)R^{27}$ and $Z^5R^{28}$. $R^{25}$, $R^{26}$, $R^{27}$ and $R^{28}$ are independently selected from H, alkyl, substituted alkyl, heteroalkyl, substituted heteroalkyl, and acyl, $Z^5$ and $Z^6$ are independently selected from O, S and NH. X is a heteroatom, e.g., selected from O and S. In an exemplary embodiment, two or more of $R^{20}$-$R^{24}$, together with the atoms to which they are bonded, are joined to form a ring system having 4-, 5-, 6-, 7-, or 8-members. The ring system is selected from substituted or unsubstituted alkyl, substituted or unsubstituted heteroalkyl, substituted or unsubstituted aryl and substituted or unsubstituted heteroaryl. In various embodiments, the ring structure is a fused ring system and, optionally, includes more than 8-members incorporated in more than one ring system.

In an exemplary embodiment, one or more of $R^{20}$-$R^{24}$ is alkoxy. In an exemplary embodiment, one or more of $R^{20}$-$R^{24}$ is $C_1$-$C_6$ alkoxy. In an exemplary embodiment, $R^{20}$-$R^{24}$ is methoxy. In an exemplary embodiment, one or more of $R^{20}$-$R^{24}$ is nitro.

An exemplary caging moiety has the structure:

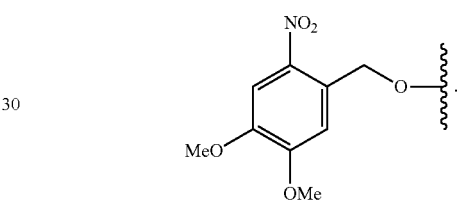

Reactive Functional Groups

The compounds of the invention are assembled from covalent bonding reactions between precursors bearing a reactive functional group, which is a locus for formation of a covalent bond between the precursors. The precursors of compounds of the invention bear a reactive functional group, which can be located at any position on the compound. The finished dye conjugates can include a further reactive functional group at any point on the molecule.

Exemplary species include a bond formed through reaction of a reactive functional group attached directly to fluorophore scaffold and a caging moiety scaffold or to a linker attached to a component (e.g., aryl ring) of a precursor component. When the reactive group is attached a substituted or unsubstituted alkyl or substituted or unsubstituted heteroalkyl linker moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with precursor components of compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
  (a) carboxyl groups and derivatives thereof including, but not limited to activated esters, e.g., N-hydroxysuccinimide esters, N-hydroxyphthalimide, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;
  (b) hydroxyl groups, which can be converted to esters, sulfonates, phosphoramidates, ethers, aldehydes, etc.
  (c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
  (d) dienophile groups, which are capable of participating in Diels-Alder reactions such as, for example, maleimido groups;
  (e) aldehyde or ketone groups, allowing derivatization via formation of carbonyl derivatives, e.g., imines, hydrazones, semicarbazones or oximes, or via such mechanisms as Grignard addition or alkyllithium addition;
  (f) sulfonyl halide groups for reaction with amines, for example, to form sulfonamides;
  (g) thiol groups, which can be converted to disulfides or reacted with acyl halides, for example;
  (h) amine or sulfhydryl groups, which can be, for example, acylated, alkylated or oxidized;
  (i) alkenes, which can undergo, for example, cycloadditions, acylation, Michael addition, etc;
  (j) epoxides, which can react with, for example, amines and hydroxyl compounds; and
  (k) phosphoramidites and other standard functional groups useful in nucleic acid synthesis.

The reactive functional groups can be chosen such that they do not participate in, or interfere with, the reactions necessary to assemble or utilize the compound of the invention. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In some embodiments, the compound includes a targeting moiety. In some embodiments, the targeting moiety is selected from a nucleic acid, a peptide, a saccharide, a lipid and a combination thereof. In some embodiments, the targeting moiety is specific for an excitable cell type. In some embodiments, the excitable cell type is selected from a neuron, a nerve cell, a lymphocyte, an endocrine secretory cell, a neuroendocrine secretory cell, a cardiac muscle cell, a smooth muscle cell, a skeletal muscle cell, and a mast cell.

In another aspect, the invention provides a composition comprising a living cell, wherein the cell has a membrane comprising a compound disclosed herein.

In some embodiments, the living cell is a mammalian cell. In some embodiments, the living cell is an excitable cell type. In some embodiments, the excitable cell type is selected from a neuron, a nerve cell, an endocrine secretory cell, a neuroendocrine secretory cell, a cardiac muscle cell, a smooth muscle cell, a skeletal muscle cell. In some embodiments, the cell is selected from a HEK293 cell and a neuron.

In some embodiments, the membrane is the plasma membrane of the cell.

In some embodiments, the cell is voltage clamped.

In some embodiments, the membrane comprises at least one ion channel, ion transporter, ion pump, or ion exchanger.

In some embodiments, the membrane of the living cell comprises an inner layer and an outer layer, wherein the A moiety of the compound disclosed herein localizes at the outer layer of said membrane, and the E moiety of the compound disclosed herein localizes at a region between the inner layer and outer layer.

In another aspect, the invention provides a method for monitoring transmembrane potential of a living cell, comprising:
  a. introducing a plurality of a compound disclosed herein into a sample comprising a living cell under conditions that permit the interaction of said plurality of compound with a plasma membrane of said cell;
  b. exciting the compound with light of a wavelength sufficient to excite the fluorophore portion of the compound described herein;
  c. detecting fluorescence emission from the plurality of the compound; and
  d. correlating said fluorescence emission to the transmembrane potential of the living cell, wherein the quenching of fluorescence emitted by the plurality of the compound is altered in response to a change in the membrane potential.

In some embodiments, the living cell is a mammalian cell.

In some embodiments, the living cell is an excitable cell type.

In some embodiments, the excitable cell type is selected from a neuron, a nerve cell, an endocrine secretory cell, a neuroendocrine secretory cell, a cardiac muscle cell, a smooth muscle cell, a skeletal muscle cell.

In some embodiments, the cell is selected from a HEK293 cell and a neuron.

In some embodiments, the membrane is the plasma membrane of said cell.

In some embodiments, the cell is voltage clamped.

In some embodiments, the membrane comprises at least one ion channel, ion transporter, ion pump, or ion exchanger.

In some embodiments, the membrane of the living cell comprises an inner layer and an outer layer, wherein the A moiety of the compound disclosed herein localizes at the outer layer of said membrane, and the E moiety of the compound disclosed herein localizes at a region between the inner layer and outer layer.

In various embodiments, the invention provides a method of identifying a test chemical that modulates transmembrane potential in at least one cell, said method comprising the steps:
  a. contacting said at least one cell with a plurality of a compound disclosed herein, wherein said cell has a membrane;
  b. exposing the membrane to said test chemical;
  c. exciting the compound with light of a wavelength sufficient to excite the fluorophore portion of the compound disclosed herein;
  d. detecting fluorescence emission of said plurality of the compound;
  e. correlating said fluorescence emission to transmembrane potential of the cell; and f. comparing said transmembrane potential to a control value, wherein a difference between said transmembrane potential and the control value is indicative of the test chemical's ability to modulate transmembrane potential of said cell.

In some embodiments, the cell is a living cell.

In some embodiments, the living cell is a mammalian cell.

In some embodiments, the living cell is an excitable cell type.

In some embodiments, the excitable cell type is selected from a neuron, a nerve cell, an endocrine secretory cell, a neuroendocrine secretory cell, a cardiac muscle cell, a smooth muscle cell, a skeletal muscle cell.

In some embodiments, the cell is selected from a HEK293 cell and a neuron.

In some embodiments, the membrane is the plasma membrane of said cell.

In some embodiments, the cell is voltage clamped.

In some embodiments, the membrane comprises at least one ion channel, ion transporter, ion pump, or ion exchanger.

In some embodiments, the membrane of the living cell comprises an inner layer and an outer layer, wherein the A moiety of the compound disclosed herein localizes at the outer layer of said membrane, and the E moiety of the compound disclosed herein localizes at a region between the inner layer and outer layer.

Drug Screening

The invention also provides methods for screening candidate agents such as potential therapeutic drugs which affect membrane potentials in biological cells. These methods involve measuring membrane potentials as described above in the presence and absence (control measurement) of the test sample. Control measurements are usually performed with a sample containing all components of the test sample except for the putative drug. Detection of a change in membrane potential in the presence of the test agent relative to the control indicates that the test agent is active. Membrane potentials can be also be determined in the presence or absence of a pharmacologic agent of known activity (i.e., a standard agent) or putative activity (i.e., a candiate agent). A difference in membrane potentials as detected by the methods disclosed herein allows one to compare the activity of the test agent to that of the standard agent. It will be recognized that many combinations and permutations of drug screening protocols are known to one of skill in the art and they may be readily adapted to use with the method of membrane potential measurement disclosed herein to identify compounds which affect membrane potentials. Use of the membrane potential determination technique disclosed herein in combination with all such methods are contemplated by this invention. In a particular embodiment, the invention offers a method of identifying a compound which modulates activity of an ion channel, pump, or exchanger in a membrane, comprising:

a. loading the cells with a plurality of the compound described herein b. exposing the cell membrane to the candidate agent;

c. exciting the plurality of compound with light of a wavelength sufficient to excite the fluorophore;

d. detecting fluorescence emission of said plurality of the compound;

e. correlating said fluorescence emission to transmembrane potential of the cell; and f. comparing said transmembrane potential to a control value, wherein a difference between said transmembrane potential and the control value is indicative of the agent's ability to modulate transmembrane potential of said cell.

In another embodiment, the invention offers a method of screening test samples to identify a compound which modulates the activity of an ion channel, pump or exchanger in a membrane, comprising:

a. loading a first set and a second set of cells with a plurality of the compound described herein;

b. optionally, exposing both the first and second set of cells to a stimulus which modulates the ion channel, pump or exchanger;

c. exposing the first set of cells to the candidate agent;

d. exciting the plurality of compound in both the first and second set of cells with light of a wavelength sufficient to excite the fluorophore;

e. detecting fluorescence emission of said plurality of the compound in both the first and second set of cells;

f. correlating said fluorescence emission to transmembrane potential of the cell for both the first and second set of cells; and g. relating the difference in membrane potentials between the first and second sets of cells to the ability of the candidate agent to modulate the activity of an ion channel, pump or exchanger in a membrane.

Ion channels of interest include, but are not limited to, sodium, calcium, potassium, nonspecific cation, and chloride ion channels, each of which may be constitutively open, voltage-gated, ligand-gated, or controlled by intracellular signaling pathways.

Biological cells which can be screened include, but are not limited to primary cultures of mammalian cells, cells dissociated from mammalian tissue, either immediately or after primary culture. Cell types include, but are not limited to white blood cells (e.g. leukocytes), hepatocytes, pancreatic beta-cells, neurons, smooth muscle cells, intestinal epithelial cells, cardiac myocytes, glial cells, and the like. The invention also includes the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel) and methods for their expression in cell lines of interest is within the knowledge of one of skill in the art (see, U.S. Pat. No. 5,436,128). Representative cultured cell lines derived from humans and other mammals include LM (TK) cells, HEK293 (human embryonic kidney cells), 3T3 fibroblasts, COS cells, CHO cells, RAT1 and HLHepG2 cells.

The screening methods described herein can be made on cells growing in or deposited on solid surfaces. A common technique is to use a microtiter plate well wherein the fluorescence measurements are made by commercially available fluorescent plate readers. The invention includes high throughput screening in both automated and semiautomated systems. One such method is to use cells in Costar 96 well microtiter plates (flat with a clear bottom) and measure fluorescent signal with CytoFluor multiwell plate reader (Perseptive Biosystems, Inc., MA) using two emission wavelengths to record fluorescent emission ratios. Suitable equipment, software, and methods for conducting the screening, including detection of fluorescence emission and correlation of fluorescence emissions to transmembrane potential of the cell, are described in the examples or as contemplated by those of skill in the art based on guidance from the disclosure provided herein. The materials and methods of the present invention are further illustrated by the examples that follow. These examples are offered to illustrate, but not to limit the claimed invention.

EXAMPLES

Example 1

Figure 4:
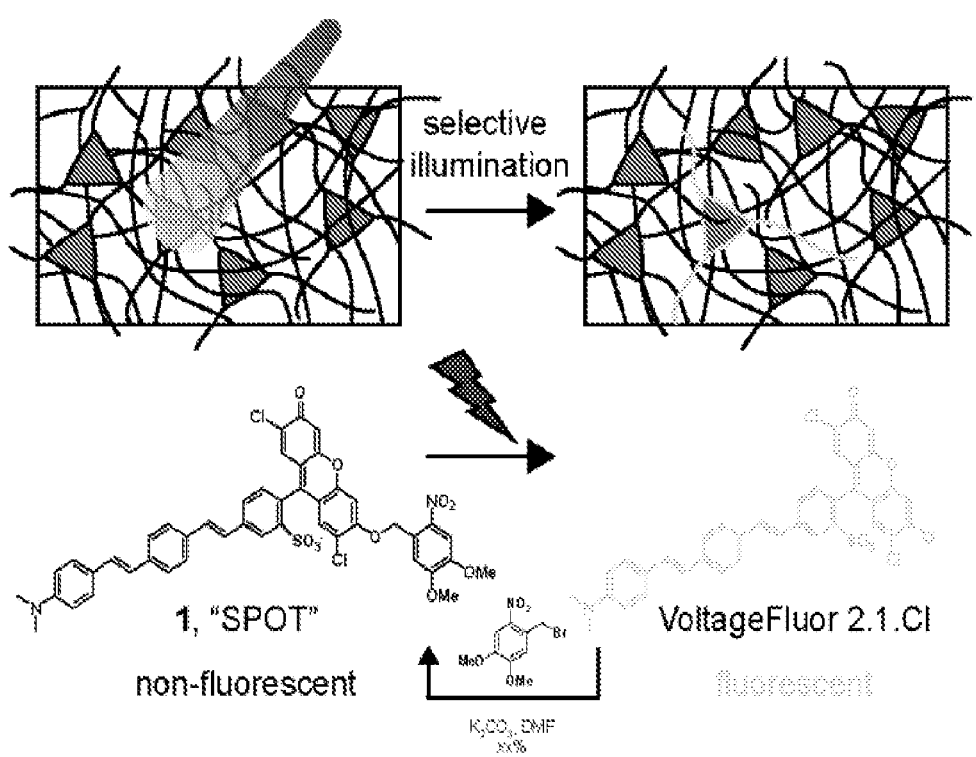
FIG. 4. Synthesis and Photoactivation of SPOT. (upper) SPOT is loaded into a sample containing neurons, glia, and astrocytes and remains non-fluorescent prior to activation. Cells of interest are demarked by cell type-specific expression of red fluorescent proteins (for example, mCherry), defining a region of interest. Illumination is provided locally to the ROI, resulting in photoactivation of SPOT and generation of bright fluorescence on the cell membrane. (lower) Synthesis of SPOT is achieved through alkylation of VoltageFluor 2.1.C1 (VF2.1.C1) under standard conditions. Photoactivation of SPOT then liberates the parent VF dye.

Exemplary compounds of the invention are synthesized from precursor fluorescent compounds, e.g., the Voltage-Fluor dyes disclosed in WO2012/159116, the disclosure of which is incorporated herein by reference in its entirety for all purposes, by appending a caging moiety to a reactive functional group of the precursor fluorescent compound. Synthesis of an exemplary caged fluorescent compound of the invention is set forth in FIG. 4.

Synthesis of 2-(2,7-dichloro-6-((4,5-dimethoxy-2-nitrobenzyl)oxy)-3-oxo-3H-xanthen-9-yl)-5-((E)-4-((E)-4-(dimethylamino)styryl)styryl)benzenesulfonic acid (SPOT)

To a 20 mL dram vial equipped with a stir bar were added 2-(2,7-dichloro-6-((4,5-dimethoxy-2-nitrobenzyl)oxy)-3-oxo-3H-xanthen-9-yl)-5-((E)-4-((E)-4-(dimethylamino)styryl)styryl)benzenesulfonic acid (VF2.1.C1, 40 mg, 0.058 mmol, 1.0 equiv.), 1-(bromomethyl)-4,5-dimethoxy-2-nitrobenzene (38 mg, 0.12 mmol, 2 equiv.), cesium carbonate (42 mg, 0.13 mmol, 2.2 equiv.) and sodium iodide (1 mg, 0.006 mmol, 0.1 equiv.). Solid reagents were taken up in 1 mL of dry DMF and the reaction was stirred at 50° C. for 17 hours, at which time the reaction was found to have gone to completion by LC-MS. Solvent was removed under reduced pressure, and the resulting crude paste was suspended in water, acidified with acetic acid and filtered. The collected precipitate was washed with water, 1:1 DCM:hexanes and $Et_2O$ to obtain SPOT as a brick red powder (49 mg, 94%). Material for biological experiments was further purified by semi-preparative HPLC. HR-ESI-MS [M-H]$^-$ calculated 877.1395, found 877.1394.

Example 2

Optical monitoring of electrical activity in the nervous system provides a powerful method for understanding brain function. In theory it can provide very precise measurements of the spatial and temporal dynamics of electrical activity in the brain. Currently methods to do this rely either on electrophysiology, which can provide extremely sensitive measurements of electrical activity in single neurons with good temporal resolution. Spatial information in a sub-cellular sense is difficult to acquire because of the requirement of bulky electrode. Information on populations of neurons is difficult to acquire because multiple electrode are required. Fluorescence imaging of $Ca^{2+}$ can provide spatial resolution at the sub- and supra-cellular level, but these signals are downstream of the action potential, difficult to resolve in fast spiking neurons, buffered by the indicators themselves, and biased toward post-threshold events. Although a variety of fluorescent probes for voltage have been developed, they suffer from either from low sensitivity or slow response times. Two major classes exist, fast and slow response dyes. Fast response dyes can temporally resolve action potentials, because they respond to voltage in the sub-microsecond time regime. However, the fractional changes can be very small (typically about 2-10%/100 mV). Slow response dyes redistribute themselves within the membrane in response to changes in membrane potential, and their concentration can change up to 10-fold in response to a Nernstian equilibrium, however, these large changes require movement of a charged dye molecule through the lipid membrane, resulting in slow response times and capacitive loading.

In contrast, a molecular wire electron transfer (eT) based optical probe provide large and fast changes in response to voltage with no capacitive loading. Increasing the sensitivity of the probe to voltage without sacrificing speed will increase its utility in monitoring voltage in brain systems. However, because small molecule dyes must be delivered to the systems of interest, i.e. they are not genetically encoded and therefore not synthesized by the cells, selective staining of neurons is not selective. As a result, signal-to-noise ratios for the measured optical changes can be quite small. Some genetically encoded voltage sensors exist, but are either too dim (Hochbaum, et al., Nat Methods, 2014), too insensitive (Mutoh, et al., ACS Chemical Neuroscience, 2012, 3:585), provide non-ideal turn-off responses to membrane depolarizations (St-Pierre, et al., Nat Neurosci, 2014; Jin, et al., Neuron, 2012, 75:779), or have the potential to add capacitive loads to membranes of interest (Mutoh, et al., ACS Chemical Neuroscience, 2012, 3:585; St-Pierre, et al., Nat Neurosci, 2014; Jin, et al., Neuron, 2012, 75:779). Small molecule dyes, in contrast are generally brighter, and VoltageFluors in particular are fast and sensitive enough to detect action potential spikes in single trials. Genetic targeting of VF dyes has not been achieved, and sparse labeling of neurons with VF dyes would increase the tractability of the approach for use in tissues, brain slices, and in vivo contexts.

Figure 1B:
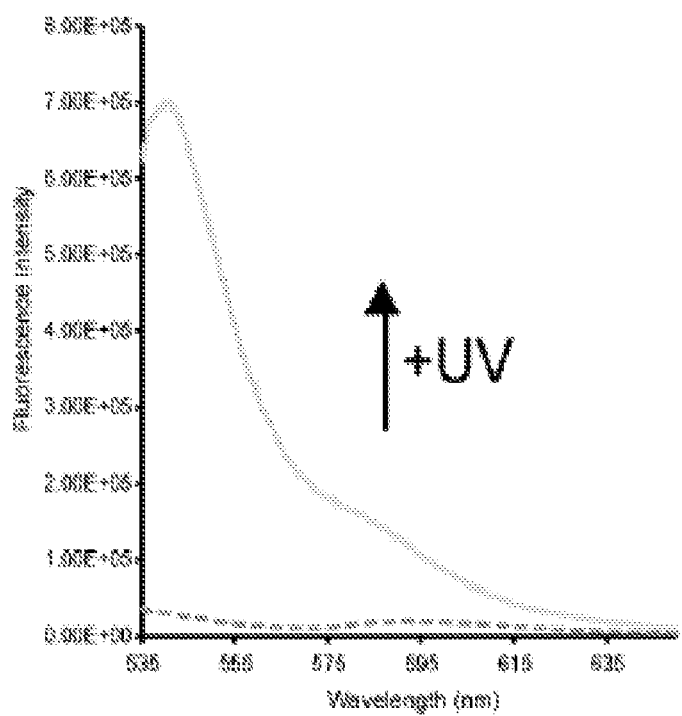
Figure 2:
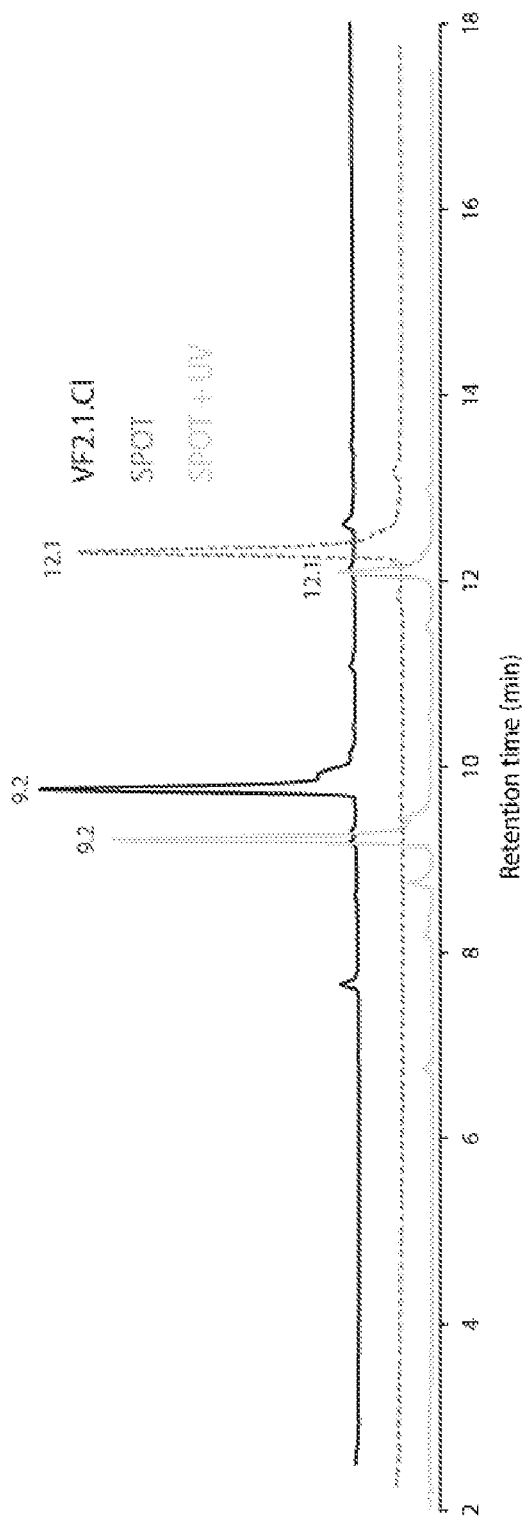
FIG. 2. Characterization of SPOT photoproducts. Irradiation of SPOT (grey dotted trace) under simulated physiological conditions (phosphate buffered saline, pH 7.0; 365 nm light) cleanly gives VF2.1.C1 (black trace, standard; green trace, UV irradiated SPOT) as detected by HPLC and mass spectrometry.
Figure 3A:
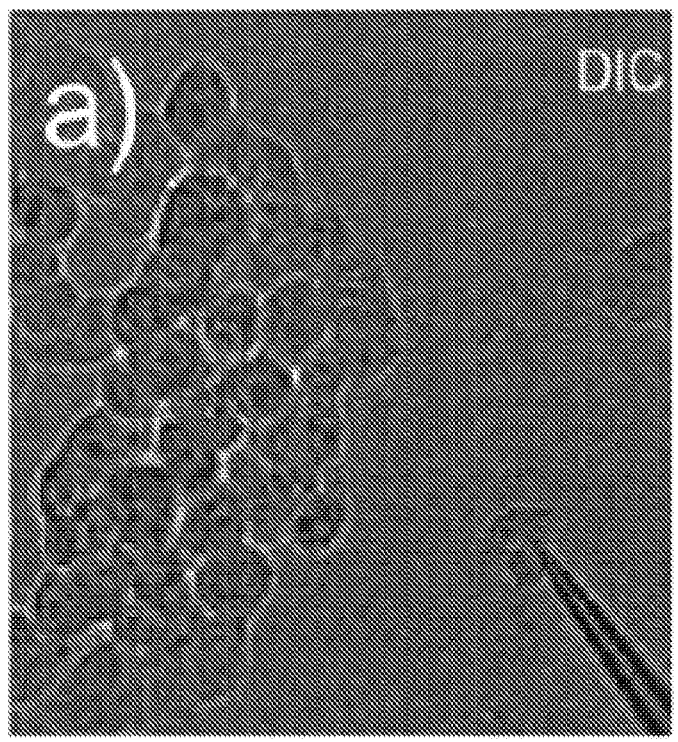
FIGS. 3A-3E. Electrophysiological characterization of photoactivated SPOT. a) DIC image of HEK cells stained with 200 nM SPOT in which a single cell is subjected to patch clamp electrophysiology. b) Fluorescence image of cells in panel a) prior to photoactivation of SPOT. c) Fluorescence image of cells in panels a) and b) following 30 seconds of UV illumination to activate SPOT. d) Fluorescence response of activated SPOT in HEK cells under voltage clamp and subjected to 50 ms depolarizing steps from −60 mV to the indicated potential. e) Plot of fractional change in activated SPOT (VF2.1.C1) fluorescence vs. final membrane potential (from −60 mV). The slope of the line indicates a voltage sensitivity of approximately 19% ΔF/F per 100 mV.
Figure 3B:
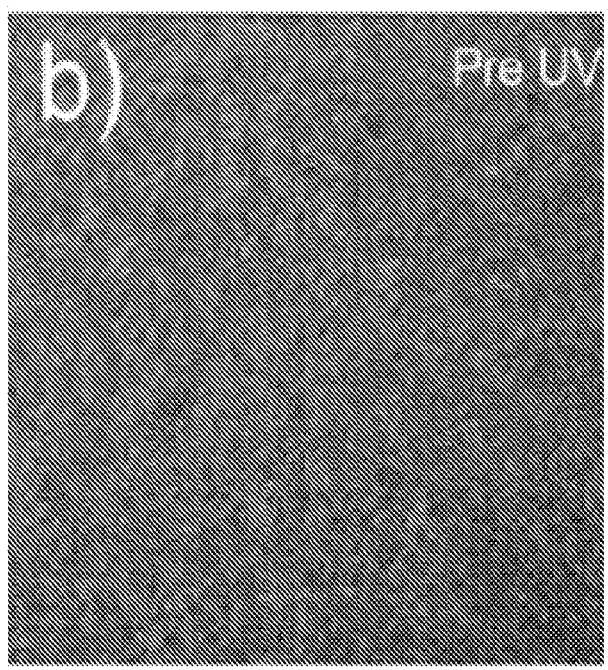
Figure 3C:
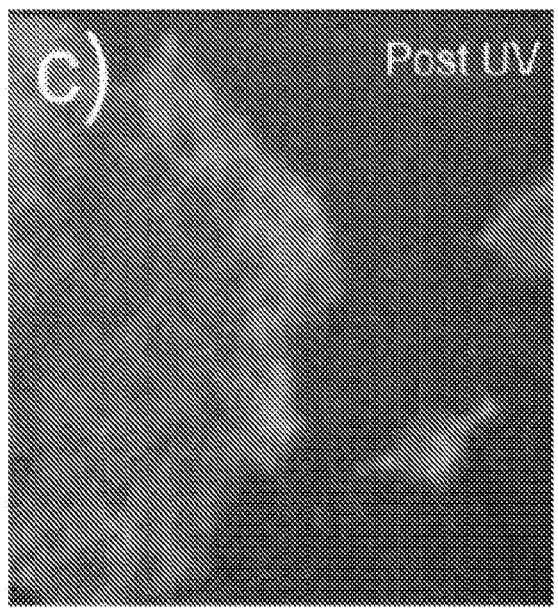
Figure 3D:
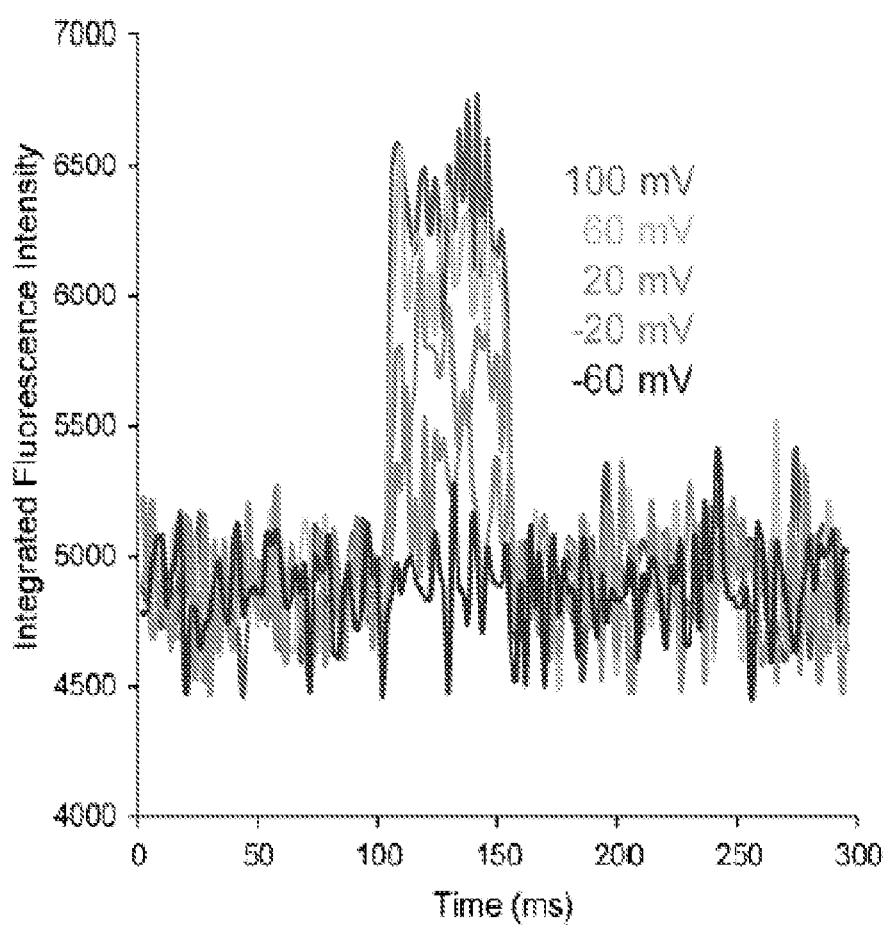
Figure 3E:
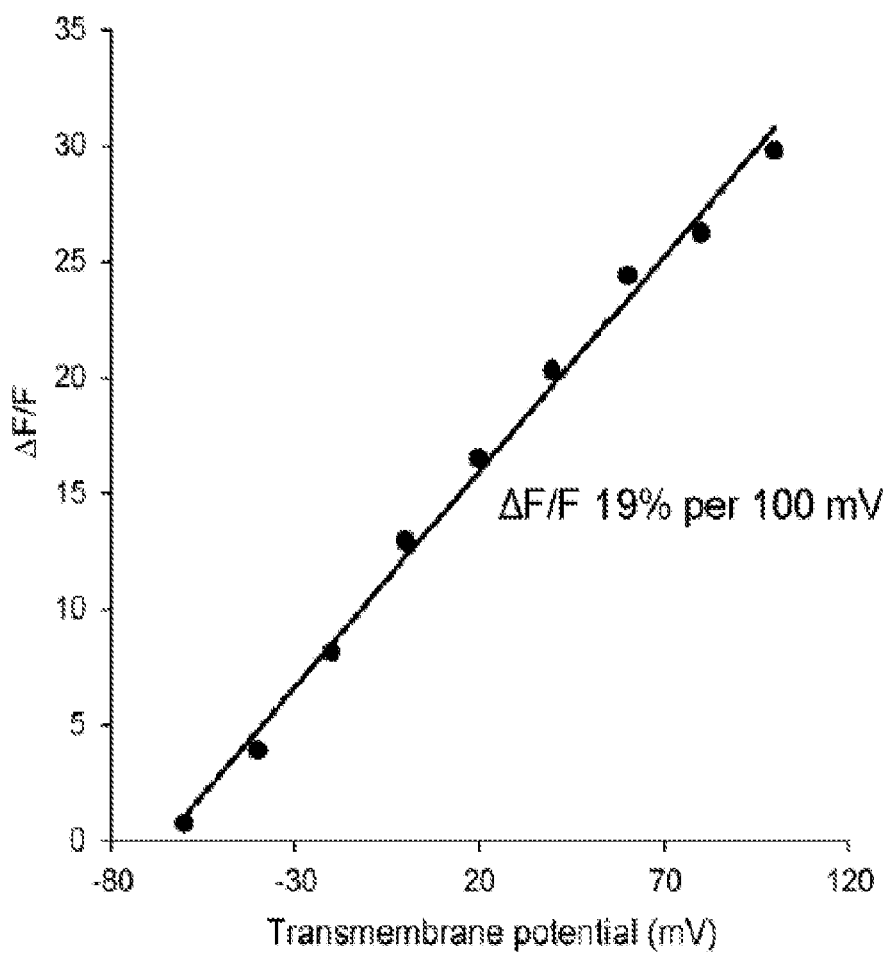

SPOT is readily available in one step from previously reported VoltageFluor compounds (Miller, et al., Natl Acad Sci USA, 2012, 109:2114). Alkylation of VF2.1.C1 with 2-nitro-4,5-dimethoxybenzylbromide in DMF provides SPOT as an analytically pure sample after purification via HPLC. Larger quantities are available through an alternate route in which the sulfonefluorescein head-group is first alkylated and then coupled to the phenylenevinylene molecular wire to give SPOT. We examined the photophysical behavior and characteristics of SPOT under simulated physiological conditions (PBS, pH 7). As synthesized, SPOT displays an absorbance profile significantly altered from the parent VF dye (FIG. 1A, grey and black traces), with a $\lambda_{max}$ centered at 400 nm attributed to the molecular wire absorbance and a minor absorbance centered at 500 nm corresponding to the alkylated fluorescein scaffold. In contrast, the free VF dye demonstrates strong absorbance at 522 nm, with a shoulder at 488 nm. Emission from SPOT is minimal (FIG. 1B, grey trace), as reflected by its low fluorescence quantum yield. UV illumination of SPOT promptly delivers VF, as measured by complete recovery of absorbance profiles characteristic of VF2.1.C1 (FIG. 1A, green and black traces) and a 25-fold increase in fluorescence emission (FIG. 1B green trace). The identity of the photoproducts of illumination were confirmed by HPLC against known standards and established the clean conversion of SPOT into VF2.1.C1 upon irradiation (FIG. 2).

Figure 1C:
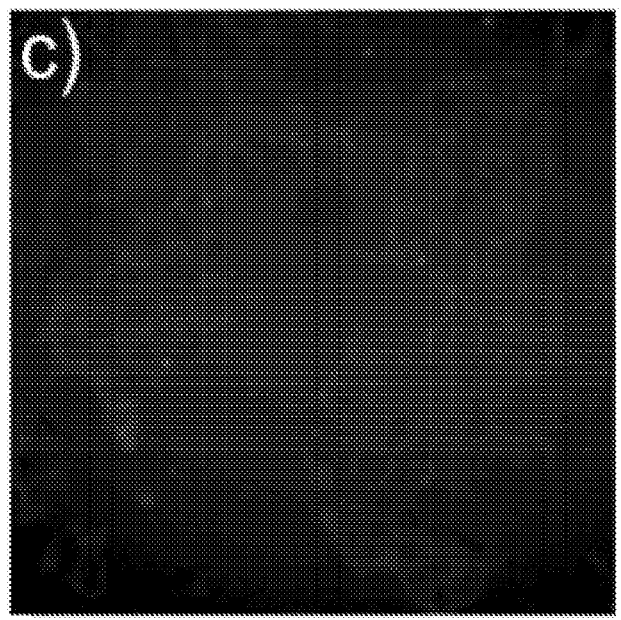
Figure 1D:
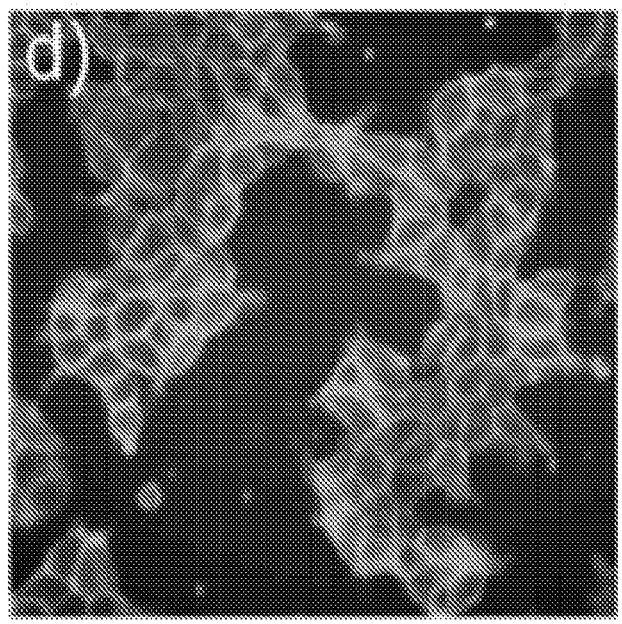
Figure 1E:
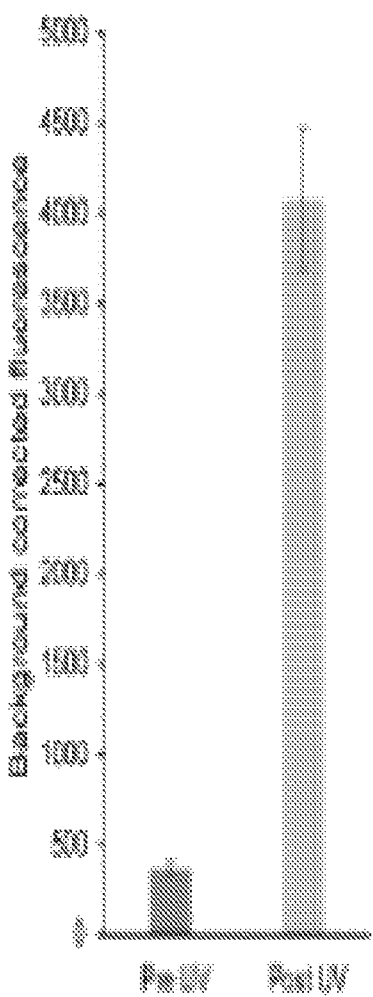

We next turned our attention to assessing the properties of SPOT in living cells. Bath application of SPOT to human embryonic kidney cells (HEK 293) resulted in very little fluorescence staining of cell membranes or soma, as expected, due to the low intrinsic brightness of SPOT (FIG. 1C). Illumination with 390 nm (30 s) light results in an immediate increase in cell membrane-associated fluorescence characteristic of VoltageFluor staining (FIG. 1D). Indicating that SPOT had localized to cell membranes and remained optically silent until photoactivation. Quantification of the mean cellular fluorescence intensity pre- and post-UV indicates that SPOT provides a 12±1.2-fold (n=3) increase in fluorescence intensity following irradiation (FIG. 1E). Membrane-associated fluorescence depends on prior UV illumination, as examination of areas of the same sample not exposed to light show very little cellular fluorescence.

However, subsequent photoactivation of this region (390 nm, 30 s) results in a similar fluorescence increase, indicating that patterns of spatially restricted light can selective photoactivate distinct cell populations. Following illumination, the cells stained with SPOT become bright and voltage-sensitive. Whole-cell patch clamp electrophysiological measurements in HEK cells reveal that post-illumination, activated SPOT has a voltage sensitivity 18% ΔF/F per 100 mV, approaching the sensitivity achieved by the parent VoltageFluor, VF2.1.C1 (FIG. 3).

SPOT is useful for interrogating systems such as brain slices and whole brains which have otherwise proved intractable for VF sensors due to non-specific background staining. We anticipate using genetically encoded fluorescent proteins, under cell-specific promoter control, to label cells of interest. SPOT would then be loaded into all cells and remain dark. The genetic marker would be used to specify a region of interest (ROI) for photoactivation. Light would be delivered to that region to photoactivate SPOT and enable optical voltage recording in that area alone. The illumination can be provide using either one or two-photon methods. The two-photon irradiation will be useful for thicker samples.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to the formula:

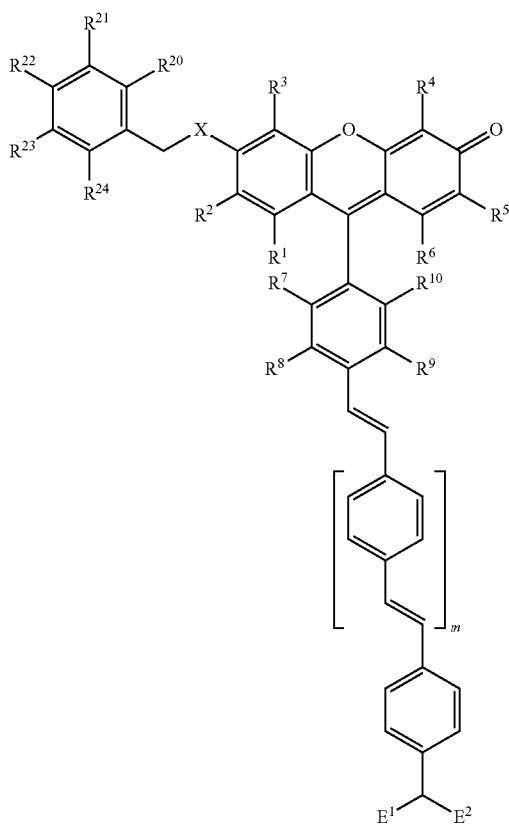

wherein
$R^1$, $R^2$, $R^3$, $R^4$, $R^5$, and $R^6$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$;

$R^7$, $R^8$, $R^9$, and $R^{10}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$, $R^{20}$, $R^{21}$, $R^{22}$, $R^{23}$, and $R^{24}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, acyl, H, $NO_2$, CN, $SO_3H$, $NR^{25}R^{26}$, and $Z^5R^{28}$ wherein
$R^{25}$, $R^{26}$ and $R^{28}$ are independently selected from H, alkyl, substituted alkyl, heteroalkyl, substituted heteroalkyl, and acyl, $Z^5$ and $Z^6$ are independently selected from O, S and NH;

X is selected from O and S wherein
two or more of $R^{20}$–$R^{24}$, together with the atoms to which they are bonded, are optionally joined to form a ring system having 4-, 5-, 6-, 7-, or 8-members, said ring system selected from substituted or unsubstituted alkyl, substituted or unsubstituted heteroalkyl, substituted or unsubstituted aryl and substituted or unsubstituted heteroaryl ring systems wherein m is an integer selected from 0, 1, 2, 3, 4, 5, 6, 7, 8, 9, 10, 11, 12, 13, 14, 15, 16, 17, 18, 19 and 20 wherein $E^1$ and $E^2$ are independently alkyl wherein
$R^{12}$ is selected from H, alkyl, substituted alkyl, heteroalkyl, substituted heteroalkyl, and $C(Z^3)R^{15}$;

$R^{13}$ and $R^{15}$ are independently selected from alkyl, substituted alkyl, heteroalkyl, substituted heteroalkyl, $OR^{16}$ and $NR^{17}R^{18}$;

wherein
$R^{16}$ is selected from H, alkyl, substituted alkyl, heteroalkyl, substituted heteroalkyl, aryl, substituted aryl, heteroaryl, substituted heteroaryl and $C(O)R^{19}$;

wherein
$R^{19}$ is selected from alkyl, substituted alkyl, heteroalkyl and substituted heteroalkyl;

$R^{11}$, $R^{13}$, $R^{17}$ and $R^{18}$ are independently selected from H, alkyl, substituted alkyl, heteroalkyl and substituted heteroalkyl;

$Z^1$ and $Z^3$ are independently selected from O, S and NH; and $Z^2$ is selected from O and S.

2. The compound of claim 1, having a structure seleceted from:

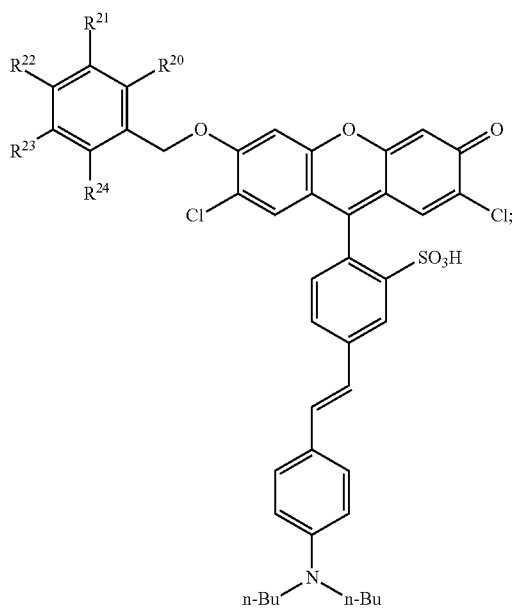

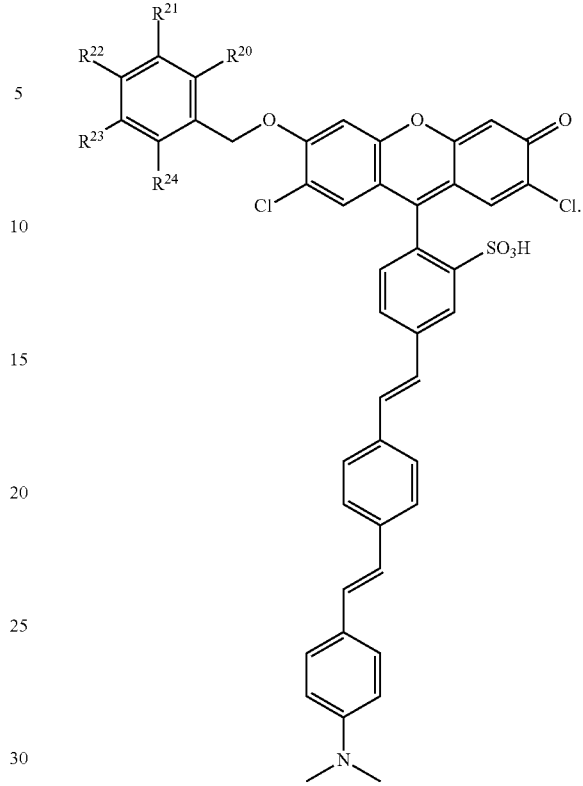

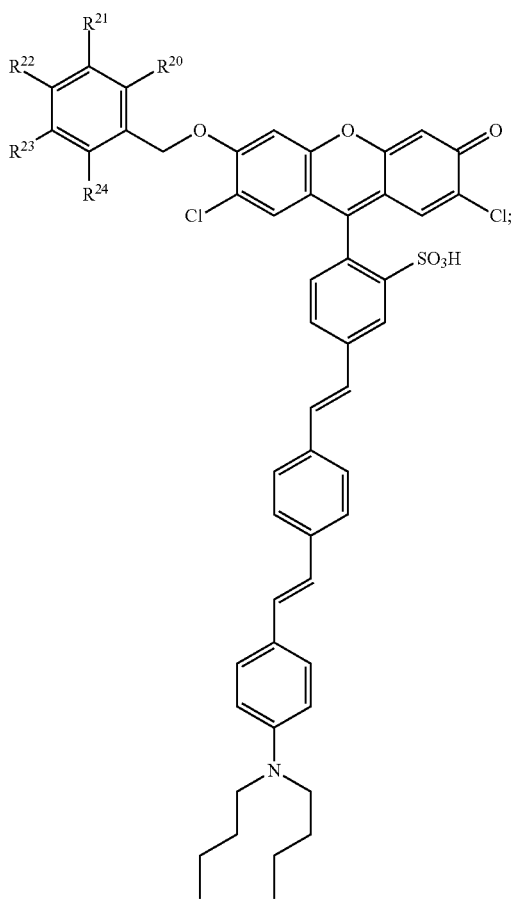
and

3. The compound of claim 1, substituted with a targeting moiety.

4. The compound of claim 3, wherein the targeting moiety is selected from a nucleic acid, a peptide, a saccharide, a lipid and a combination thereof.

5. The compound of claim 3 wherein the targeting moiety is specific for an excitable cell type.

6. The compound of claim 5, wherein said excitable cell type is selected from a neuron, a nerve cell, an endocrine secretory cell, a neuroendocrine secretory cell, a cardiac muscle cell, a smooth muscle cell, and a skeletal muscle cell.

7. A composition comprising a living cell, said cell having a membrane comprising the compound according to claim 1.

8. The composition of claim 7, wherein said living cell is a mammalian cell.

9. A method for monitoring transmembrane potential of a living cell, comprising:
 a. introducing a plurality of the compound according to any of claims 1, 2, and 3-5 into a sample comprising a living cell under conditions that permit the interaction of said plurality of compound with a plasma membrane of said cell;
 b. exciting the compound with light of a wavelength sufficient to excite the fluorophore;
 c. detecting fluorescence emission from said plurality of the compound; and
 d. correlating said fluorescence emission to the transmembrane potential of the living cell,
wherein the quenching of fluorescence emitted by said plurality of the compound is altered in response to a change in the membrane potential.

10. The method of claim 9, wherein said living cell is a mammalian cell.

11. The method of claim 9, wherein said living cell is an excitable cell type.

12. The method of claim 11, wherein said excitable cell type is selected from a neuron, a nerve cell, an endocrine secretory cell, a neuroendocrine secretory cell, a cardiac muscle cell, a smooth muscle cell, and a skeletal muscle cell.

13. The method of claim 9, wherein said cell is selected from a HEK293 cell and a neuron.

14. A method of identifying a candidate agent that modulates transmembrane potential in at least one cell, said method comprising the steps:
   a. contacting said at least one cell with a plurality of the compound according to claims 1, 2, and 3-5, wherein said cell has a membrane;
   b. exposing the membrane to said agent;
   c. exciting the plurality of compound with light of a wavelength sufficient to excite the fluorophore;
   d. detecting fluorescence emission of said plurality of the compound;
   e. correlating said fluorescence emission to transmembrane potential of the cell; and
   f. comparing said transmembrane potential to a control value, wherein a difference between said transmembrane potential and the control value is indicative of the agent's ability to modulate transmembrane potential of said cell.

15. The compound of claim 1, wherein $E^1$ and $E^2$ are independently selected from unsubstituted $C_1$-$C_6$ alkyl.

16. The compound of claim 1, wherein $E^1$ and $E^2$ are independently selected from methyl and butyl.

17. The compound of claim 1, wherein $E^1$ and $E^2$ are butyl.

18. The compound of claim 1, wherein $E^1$ and $E^2$ are n-butyl.

19. The compound of claim 1, wherein one or more of $R^{20}$-$R^{24}$ is alkoxy.

20. The compound of claim 1, wherein one or more of $R^{20}$-$R^{24}$ is $C_1$-$C_6$ alkoxy.

21. The compound of claim 1, wherein $R^{20}$-$R^{24}$ is methoxy.

22. The compound of claim 1, wherein one or more $R^{20}$-$R^{24}$ is nitro.

23. The compound of claim 1, wherein

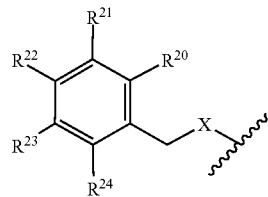

has the structure:

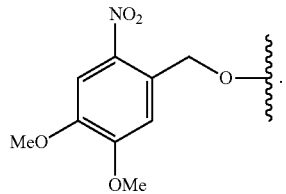 [SMILES: *OCc1cc(OC)c(OC)cc1[N+](=O)[O-]]

* * * * *

UNITED STATES PATENT AND TRADEMARK OFFICE
CERTIFICATE OF CORRECTION

Page 1 of 1

PATENT NO. : 10,837,968 B2
APPLICATION NO. : 15/514786
DATED : November 17, 2020
INVENTOR(S) : Evan Miller et al.

It is certified that error appears in the above-identified patent and that said Letters Patent is hereby corrected as shown below:

In the Specification

In Column 1, after Line 5, the paragraph below should read:
SPONSORED RESEARCH AND DEVELOPMENT
This invention was made with Government support under NS078561 awarded by the National Institutes of Health. The Government has certain rights in the invention.

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*